US005656602A

United States Patent [19]
Tseng et al.

[11] Patent Number: 5,656,602
[45] Date of Patent: Aug. 12, 1997

[54] PLA$_2$ INHIBITORY COMPOUNDS

[75] Inventors: Albert Peng Sheng Tseng, Epping; Adam Inglis, Strathmore; Kieran Scott, Waverley, all of Australia

[73] Assignee: Garvan Institute of Medical Research, Darlinghurst, Australia

[21] Appl. No.: 170,360

[22] PCT Filed: Jul. 6, 1992

[86] PCT No.: PCT/AU92/00333

§ 371 Date: Mar. 3, 1994

§ 102(e) Date: Mar. 3, 1994

[87] PCT Pub. No.: WO93/01215

PCT Pub. Date: Jan. 21, 1993

[30] Foreign Application Priority Data

Jul. 4, 1991 [AU] Australia ................... PK7058

[51] Int. Cl.$^6$ .................. A61K 38/00; C07K 7/00
[52] U.S. Cl. ............. 514/17; 514/11; 530/317; 530/329; 530/330
[58] Field of Search .................. 530/317, 329, 530/330; 514/11, 17

[56] References Cited

U.S. PATENT DOCUMENTS

| | | | |
|---|---|---|---|
| 4,742,155 | 5/1988 | Umezawa et al. | 530/317 |
| 4,792,555 | 12/1988 | McGregor et al. | 514/255 |
| 4,895,931 | 1/1990 | Okazaki et al. | 530/326 |

FOREIGN PATENT DOCUMENTS

| | | |
|---|---|---|
| 288965 | 4/1988 | European Pat. Off. . |
| 397679 | 6/1989 | European Pat. Off. . |

OTHER PUBLICATIONS

Merck Manual, Fifteenth Edition, Merck & Co., Rahway, NJ (1987). See pp. 65–67.
Gardella, T. et al. (1991) Mutational analysis of the receptor-activating region of human parathyroid hormone. *J. Biol. Chem.* 266 (20), 13141–6. See abstract.
Tomatis, R. et al. (1978) Studies on trypsin inhibitors. Part VIII. *Int. J. Pept. Protein Res.* 11, 269–281. See abstract.
Guggi, A. et al. (1976) Studies on trypsin inhibitors. Part IV. *Int. J. Pept. Protein Res.* 8, 97–105. See abstract.
Baev, V. et al. (1978) Synthesis and biological activity of luliberin and its analogs. *Bioorg. Khim.* 4(4), 489–99. See abstract.
Stewart, F. (1969) Synthesis of peptide derivatives related to evolidin *Aust. J. Chem.* 22(12), 2663–71. See abstract.
*Biotechnology Newswatch*, Aug. 1, 1994, pp. 1 and 4.
*The Washington Post*, Jan. 19, 1993, p. D3.
Cross, A. et al. (1993) Choice of bacteria in animal models of sepsis. *Infection and Immunity* 61, 2741–2747. See entire article.
Patent Abstracts of Japan No. J 63–255298(A) to Yamanouchi.
Scott, et al., *Science*, vol. 250, pp. 1541–1546, Dec. 1990.
Kramer, et al., *J. Biol. Chem.*, vol. 264, pp. 5768–5775, Apr. 1989.
Bouchier, et al., *Biochem. Biophys. Acta*, vol. 1088, pp. 401–408, 1991.
Scott, et al., *Science*, vol. 250, pp. 1563–1566, Dec. 1990.
White et al., *Science*, vol. 250, pp. 1560–1563, Dec. 1990.
Seilheimer, et al., *J. Biol. Chem.* vol. 264, pp. 5335–5338, Apr. 1989.
Johnson, et al., *Adv. Exp. Med. Biol.*; PLA 2 Role and Function in Inflammation, P. Y. K. Wong ed., Plenum Press, pp. 17–34, 1990.
Renetseder, et al., *J. Biol. Chem.*, vol. 260, pp. 11627–11634, Sep. 1985.

*Primary Examiner*—Michael P. Woodward
*Assistant Examiner*—Benet Prickril
*Attorney, Agent, or Firm*—Rothwell, Figg, Ernst & Kurz

[57] ABSTRACT

The present invention provides peptides and compounds which inhibit the enzyme activity of Type II phospholipases A$_2$. The preferred compounds are pentapeptides. Where the phospholipase is human Type II phospholipase A$_2$ the preferred peptides are FLSYK and KFLSY.

9 Claims, 7 Drawing Sheets

| Exon 2: | Type | 1 | 10 | 20 | 30 | 40 |
|---|---|---|---|---|---|---|
| PORCINE | I | ALWQFRSMIKCAIPGSHPLMDFNNYGCYCGLGGSGTPVDELDR | | | | |
| RAT | I | AVWQFRNMIKCTIPGSDPFREYNNYGCYCGLGGSGTPVDDLDR | | | | |
| HUMAN | I | AVWQFRKMIKCVIPGSDPFLEYNNYGCYCGLGGSGTPVDELDK | | | | |

```
                    *    *            *** **
```

| | | | | | | |
|---|---|---|---|---|---|---|
| HUMAN | IIA | NLVNFHRMIK-LTTGKEAALSYGFYGCHCGVGGRGSPKDATDR | | | | |
| RAT | IIA | SLLEFGQMIL-FKTGKRADVSYGFYGCHCGVGGRGSPKDATDE | | | | |
| PORCINE | IIA | DLLNERKMIK-LKTGKAPVPNYAFYGCYCGLGGKGSPKDATD? | | | | |
| RABBIT | IIA | HLLDERKMIR-YTTGKEATTSYGAYGCHCGVGGRGAPK?A | | | | |

| Exon 3: | | 44 | 50 | 60 | 70 | 80 | 85 |
|---|---|---|---|---|---|---|---|
| PORCINE | I | CCETHDNCYRDAKNLDSCKFLVDNPYTESYSYSCSNTEITCN | | | | | |
| RAT | I | CCQTHDHCYNQAKKLESCKFLIDNPYTNTYSYKCSGNVITCS | | | | | |
| HUMAN | I | CCQTHDNCYDQAKKLDSCKFLLDNPYTHTYSYSCSGSAITCS | | | | | |

```
                         **
```

| | | | | | | | |
|---|---|---|---|---|---|---|---|
| HUMAN | IIA | CCVTHDCCYKRLEKR-GC-----GTKFLSYKFSNSGSRITC- | | | | | |
| RAT | IIA | CCVTHECCYNRLEKS-GC-----GTKFLTYKFSYRGGQISCS | | | | | |
| PORCINE | IIA | CCAAH | | | | | |
| RABBIT | IIA | KFLSYKFSMK | | | | | |

| Exon: 4 | | 86 | 90 | 100 | 110 | 120 | 130 |
|---|---|---|---|---|---|---|---|
| PORICINE | I | SKNNACEAFICNCDRNAAICFSKAPYNKEHK-NLDTKKYC | | | | | |
| RAT | I | DKNNDCESFICNCDRQAAICFSKVPYNKEYK-DLDTKKHC | | | | | |
| HUMAN | I | SKNKECEAFICNCDRNAAICFSKAPYNKAHK-NLDTKKYCQS | | | | | |

```
                          **
```

| | | | | | | | |
|---|---|---|---|---|---|---|---|
| HUMAN | IIA | AKQDSCRSQLCECDKAAATCFARNKTTYNKKYQYYSNKHCRGSTPRC | | | | | |
| RAT | IIA | TNQDSCRKQLCQCDKAAAECFSRNKKSYSLKYQFYPNKFCK??TPSC | | | | | |
| RABBIT | IIA | KAAAACF       QFYPANRCSGRPPSC | | | | | |

FIG.1

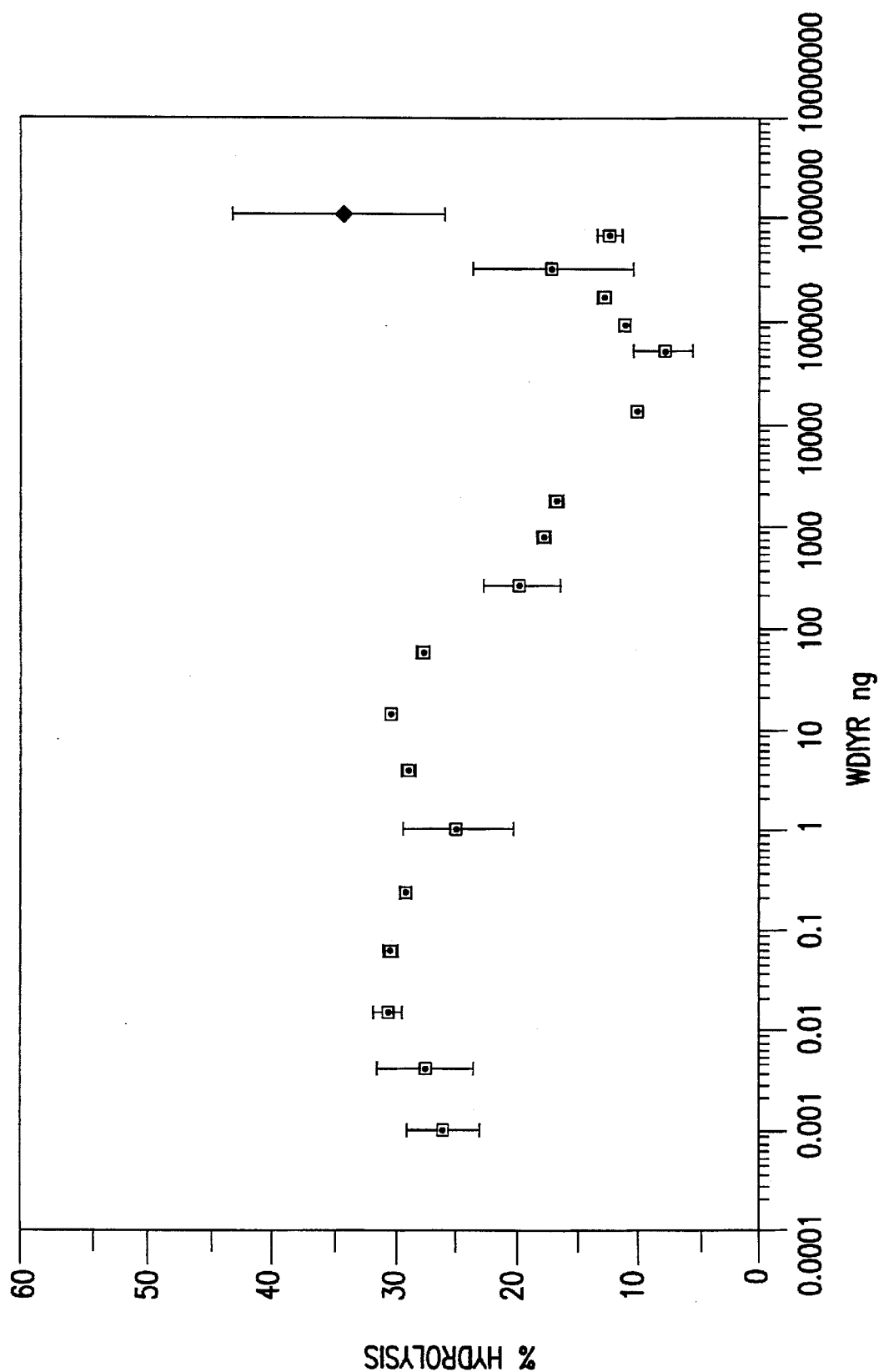

PLA₂ INHIBITORY COMPOUNDS

FIELD OF THE INVENTION

The present invention relates to peptides which inhibit the enzymatic activity of phospholipases A₂ (PLA₂s) and illustrated with peptides which inhibit the activity of Type II PLA₂'s particularly synovial PLA₂ and snake PLA₂ (*Crotalus durissus* and *Crotalus atrox*). In addition, the present invention relates to pharmaceutical composition including, as the active ingredient these peptides and to methods of treatment involving the administration of this composition.

BACKGROUND OF THE INVENTION

Phospholipases A₂ constitute a diverse family of enzymes with two subclasses (Type I and Type II) (FIG. 1), based on the positions of the disulphide bonds in the molecules while bee venom PLA₂ constitutes a third substantially distinct class of PLA₂. X-ray crystallography has revealed that the segments comprising the functional substructure of the enzyme is similar in classes. This similarity is particularly striking when the structurally-related Type I/II enzymes are compared with bee venom enzyme (2). PLA₂ hydrolyses the sn-2 acyl ester bond of phosphoglycerides initiating the release of fatty acid precursors of inflammatory eicosanoids. Human synovial PLA₂ (a Type II molecule) has recently been isolated and identified (3). The same PLA 2 has been implicated in the pathogensis of several inflammatory diseases in humans such as rheumatoid arthritis and Gram negative septic shock (7;8).

Murine, inhibitory monoclonal antibodies raised against synovial PLA₂ have demonstrated pre-clinical efficacy. Accordingly, there is interest in the development of compositions which inhibit the enzymatic activity of PLA₂.

Tryptic digestion of human synovial PLA₂ and subsequent separation and analysis of the fragments by EPLC gave a very interesting and unexpected result for one of the peaks in that it contained two peptides; one a heptapeptide (the N-terminal peptide) and the other a pentapeptide, FLSYK (SEQ ID NO:8) (corresponding to residues 70–74 in other PLA₂ molecules, based on three-dimensional structural "homology" of mammalian PLA₂ amino acid sequences (1,4)). The pentapeptide was found in an earlier eluting, fully resolved peak (as expected). Since the HPLC system failed to fully resolve these two peptides in the latter peak, these data suggest that the two peptides had a strong affinity for one another and raised questions as to the structural implications of this. X-ray diffraction studies (5,6) have shown that amino acid residues in the two peptides are close to the active site of the enzyme and are important in forming or stablising the channel in which the 1,2-diacyl-3-sn-phosphoglyceride substrate is precisely positioned for hydrolysis of the 2-ester bond. The first turn of the N-terminal helix (residues 1 to 12) is stablised by a hydrogen bond network provided by the N-terminus and residue 4, elements of residues 69 to 71 and a water mediated link to the catalytic residues; residues 2 and 5 form the "floor" of the channel, residue 9 forms the right wall and the left wall is formed by residue 69 (either tyrosine or lysine usually) which is predicted to move after the substrate has docked and to form a hydrogen bond with the sn-3 phosphate of the substrate. The chemical evidence of the strong interactions between the heptapeptide and the pentapeptide prompted the supposition that the PLA₂ activity may be inhibited in the presence of either one of these peptides.

Using synthetic peptide chemistry the present inventors have prepared the pentapeptide FLSYK and demonstrated that addition of it to the assay medium decreased the enzyme activity of human synovial PLA₂ (FIG. 2a). Furthermore, it has been demonstrated that the pentapeptide that occupies the 70–74 region of snake PLA₂ (WDIYR) also inhibited the activity of snake PLA₂ (see FIG. 3b). It is believed that this inhibition is mediated by the peptide binding to the amino terminal end of the enzyme and blocking the reaction either by blocking the substrate access to the hydrophobic channel or by distorting the structure sufficiently to prevent correct orientation of the substrate.

SUMMARY OF THE INVENTION

Accordingly, in a first aspect the present invention consists in a linear or cyclic peptide of at least 5 residues which inhibits the enzymatic activity of human synovial PLA₂, the peptide having the following formula:

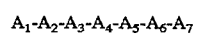

$$A_1\text{-}A_2\text{-}A_3\text{-}A_4\text{-}A_5\text{-}A_6\text{-}A_7$$

in which $A_1$ is hydrogen or one or two naturally occurring amino acids $A_2$ is F or Y or W or absent $A_3$ is L or V or I or M $A_4$ is S or T $A_5$ is Y or F or W $A_6$ is K or R or H or absent $A_7$ is OH or one or two naturally occurring amino acids.

In a preferred embodiment the peptide is a pentapeptide.

In another preferred embodiment of the present invention $A_1$ is H and $A_7$ is OH.

In a further preferred embodiment of the present invention the peptide is FLSYK (SEQ ID NO:8) or KFLSY (SEQ ID NO:9) and most preferably FLSYK.

In a second aspect the present invention consists in a linear or cyclic peptide of at least 5 residues which inhibits the enzymatic activity of *Crotalus durissus* PLA₂, the peptide having the following formula:

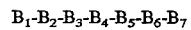

$$B_1\text{-}B_2\text{-}B_3\text{-}B_4\text{-}B_5\text{-}B_6\text{-}B_7$$

in which $B_1$ is hydrogen or one or two naturally occurring amino acids $B_2$ is W or F or Y or absent $B_3$ is D or E $B_4$ is I or V or L or M $B_5$ is Y or F or W $B_6$ is R or K or H or absent $B_7$ is OH or one or two naturally occurring amino acids.

In a preferred embodiment the peptide is a pentapeptide.

In another preferred embodiment of the present invention $B_1$ is H and $B_7$ is OH.

In a further preferred embodiment of the present invention the peptide is WDIYR (SEQ ID NO:10).

In a third aspect the present invention consists in a linear or cyclic peptide of at least 5 residues which inhibits the enzymatic activity of *Crotalus atrox* PLA₂, the peptide having the following formula:

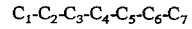

$$C_1\text{-}C_2\text{-}C_3\text{-}C_4\text{-}C_5\text{-}C_6\text{-}C_7$$

in which $C_1$ is hydrogen or one or two naturally occurring amino acids $C_2$ is T or S or absent $C_3$ is V or I or L or M $C_4$ is S or T $C_5$ is Y or F or W $C_6$ is T or S or absent $C_7$ is OH or one or two naturally occurring amino acids.

In a preferred embodiment the peptide is a pentapeptide.

In another preferred embodiment of this aspect of the present invention $C_1$ is H and $C_7$ is OH.

In a further preferred embodiment of this aspect of the present invention the peptide is TVSYT (SEQ ID NO:11).

As will be clear to those skilled in the art from the disclosure provided herein, the peptides of the first and second aspect of the present invention illustrate how the enzymatic activity of other $PLA_2$s may be inhibited. This inhibition may be achieved by compounds which interact with the N-terminal amino acid sequence of the $PLA_2$ molecule in a manner such that the channel into which the phospholipid diffuses prior to catalytic cleavage is destabilized.

Accordingly, in a fourth aspect the present invention consists in a compound which inhibits the enzymatic activity of phospholipase $A_2$, the compound being characterized in that it interacts with the N-terminal amino acid sequence of the phospholipase $A_2$ such that the channel into which the phospholipid diffuses prior to catalytic cleavage is either blocked or destabilized.

In a preferred embodiment of the present invention the $PLA_2$ is human $PLA_2$ and the compound is a peptide.

In a preferred embodiment of the present invention the peptide has the amino acid sequence FLSYK or KFLSY.

As will be clear to those skilled in the art, the present inventors have found that the enzymatic activity of a phospholipase $A_2$ can be inhibited by a peptide having a sequence corresponding to a sequence selected from the region of residues 69 to 75 of the phospholipase 2.

Accordingly, in a fifth aspect the present invention consists in a peptide of 5 or 6 residues which inhibits the enzymatic activity of a phospholipase $A_2$, the peptide having an amino acid sequence corresponding to a sequence selected from the region of residues 69–75 of the phospholipase $A_2$.

In a preferred embodiment this aspect of the present invention the peptide is a pentapeptide and has an amino acid sequence corresponding to the sequence from residue 69–73 or 70–74 of the phospholipase $A_2$.

In a further preferred embodiment of the present invention the phospholipase $A_2$ is human phospholipase $A_2$.

In a sixth aspect the present invention consists in a composition for use in treating a subject suffering from septic shock rheumatoid arthritis and/or other inflammatory diseases, the composition comprising a therapeutically acceptable amount of peptide or compound of the first, fourth or fifth aspect of the present invention and a pharmaceutical acceptable sterile carrier.

In a seventh aspect the present invention consists in a method of treating septic shock and/or inflammatory disease in a subject comprising administering to the subject the composition of the sixth aspect of the present invention.

It will be appreciated by those skilled in the art that a number of modifications may be made to the peptides of the present invention without deleteriously effecting the biological activity of the peptide. This may be achieved by various changes, such as insertions, deletions and substitutions, either conservative or non-conservative in the peptide sequence where such changes do not substantially decrease the biological activity of the peptide. By conservative substitutions the intended combinations are:

G, A; V, I, L, M; D, E; N, Q; S, T; K, R, H; and F, Y, W.

It may also be possible to add various groups to the peptide of the present invention to confer advantages such as increased potency or extended half life in vivo, without substantially decreasing the biological activity of the peptide.

It is intended that such modifications to the peptide of the present invention which do not result in a decrease in biological activity are with in the scope of the present invention.

DETAILED DESCRIPTION OF THE PRESENT INVENTION

In order that the nature of the present invention may be more clearly understood, preferred forms thereof will now be described with reference to the following examples and Figures, in which:

FIG. 1 shows mammalian $PLA_2$ amino acid sequences (SEQ ID NOS. 1, 2, 3, 4, 5, 6 and 7).

Figure 2A:
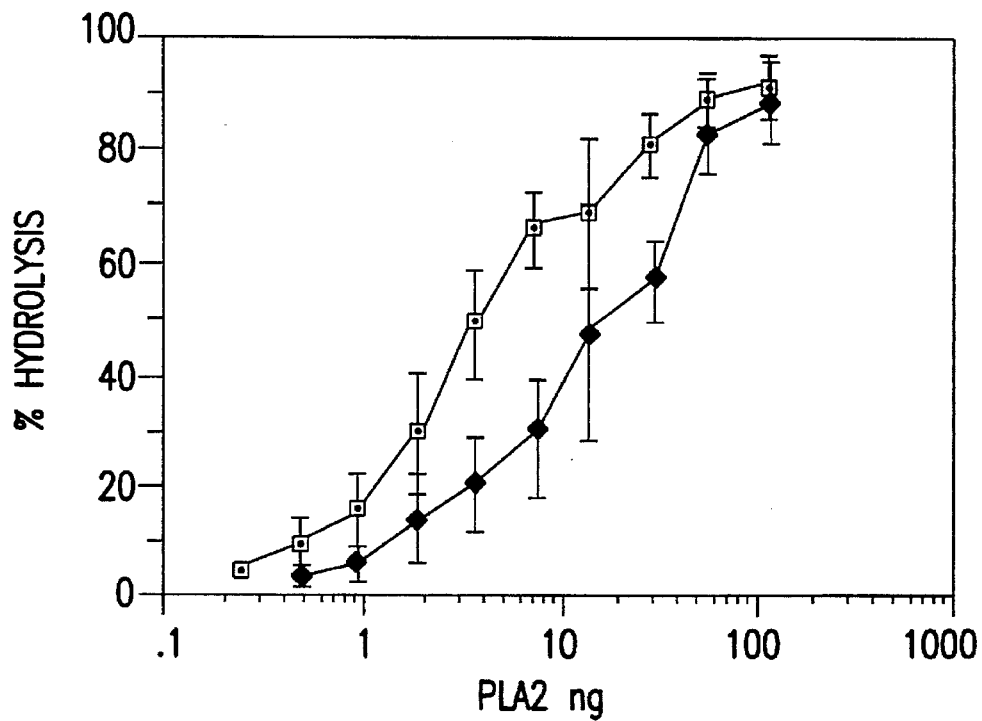
Figure 2B:
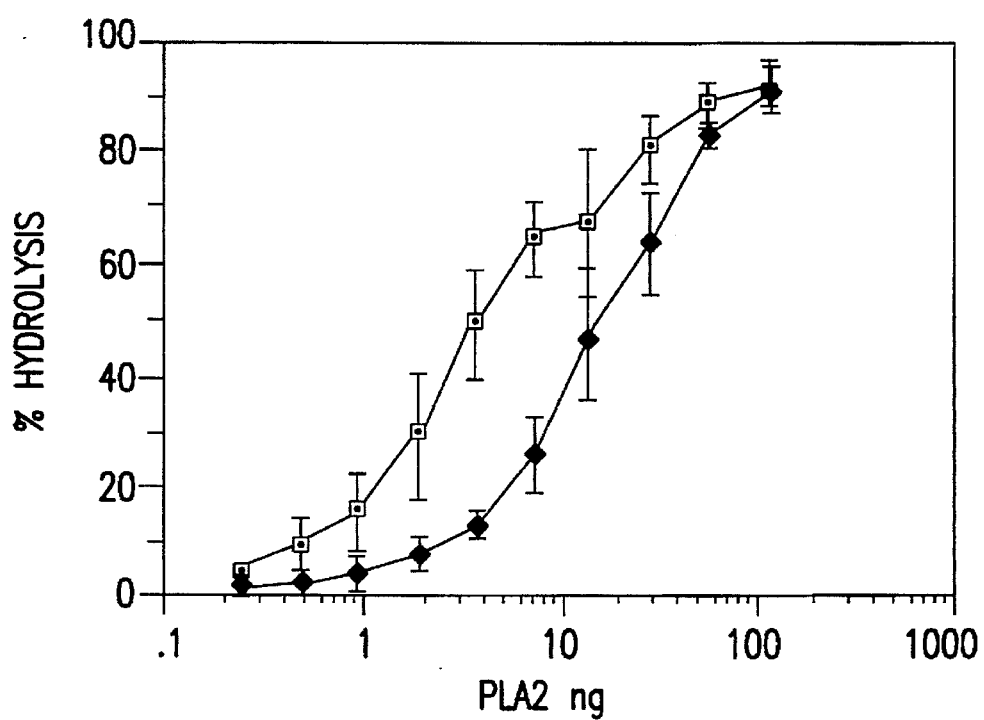
Figure 2C:
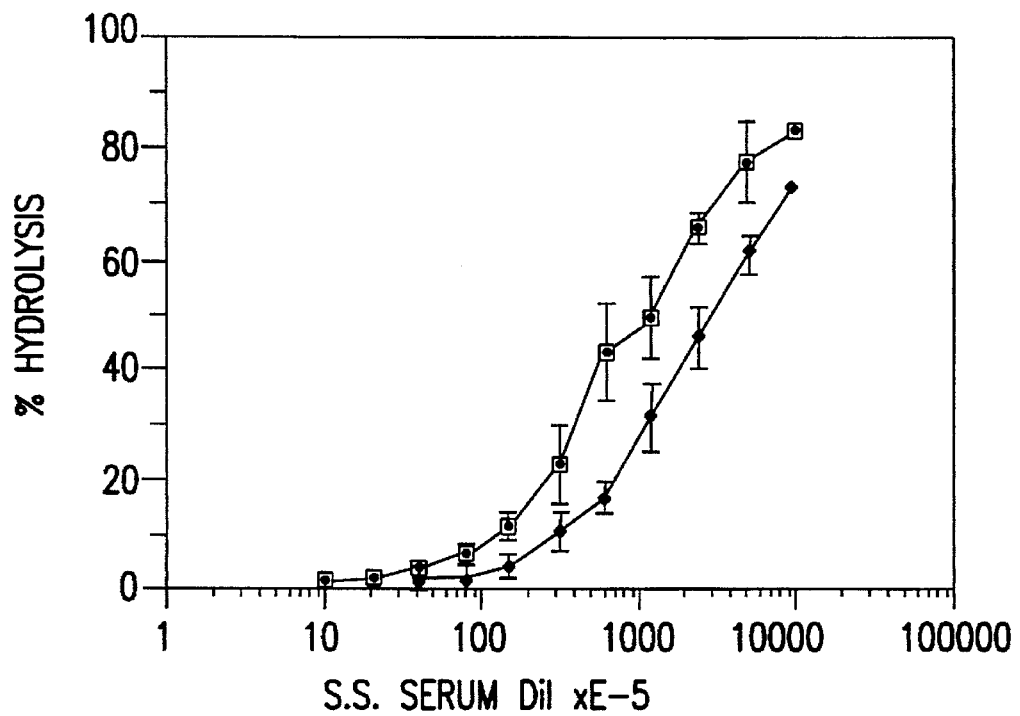

FIG. 2: Inhibition of human $PLA_2$ using the peptide FLSYK.

FIG. 2(a) was obtained using a peptide from a tryptic digest of the enzyme (n=7 ▫ control ♦ inhibitor), 2(b) and 2(c) with a synthetic peptide n=11 ▫ control ♦ inhibitor ▫ control ♦ inhibitor, respectively. The synthetic peptide also inhibits the enzyme in septic shock serum [FIG. 2(c)].

Figure 3A:
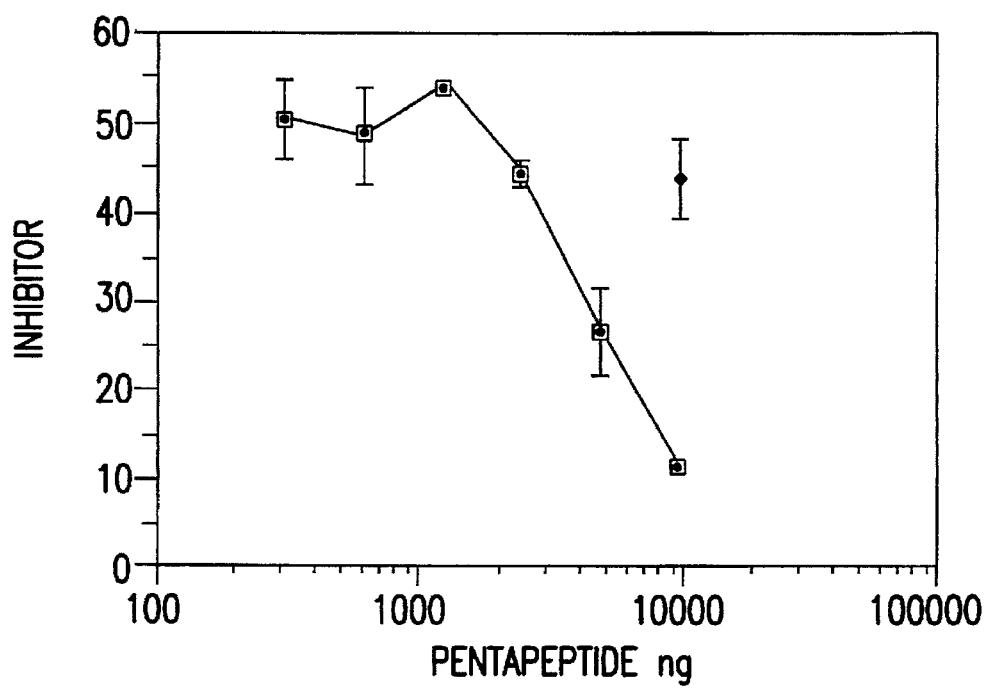
Figure 3B:
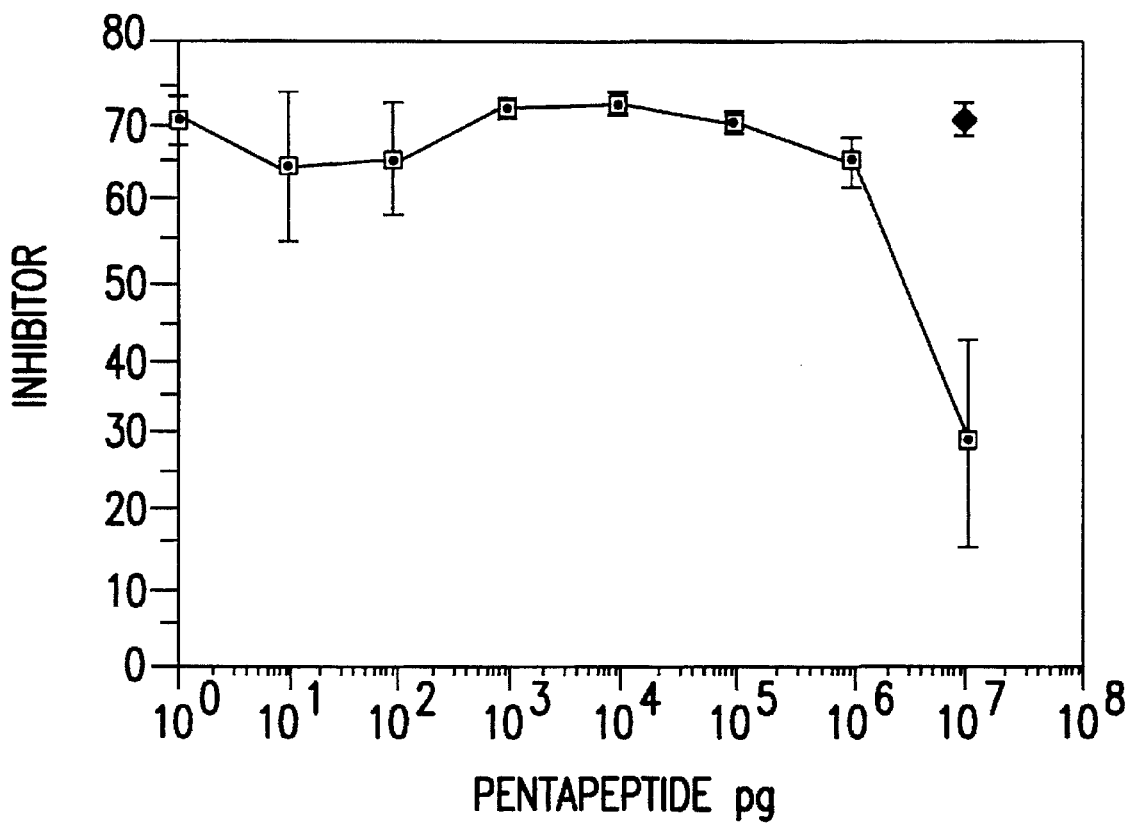

FIG. 3: Dose response curves showing increasing inhibitor with increasing amount of FLSYK and human recombinant Type II $PLA_2$ (3a ▫ inhibitor ♦ control) and in $PLA_2$ in septic shock serum (3b ▫ inhibitor ♦ control).

Figure 4A:
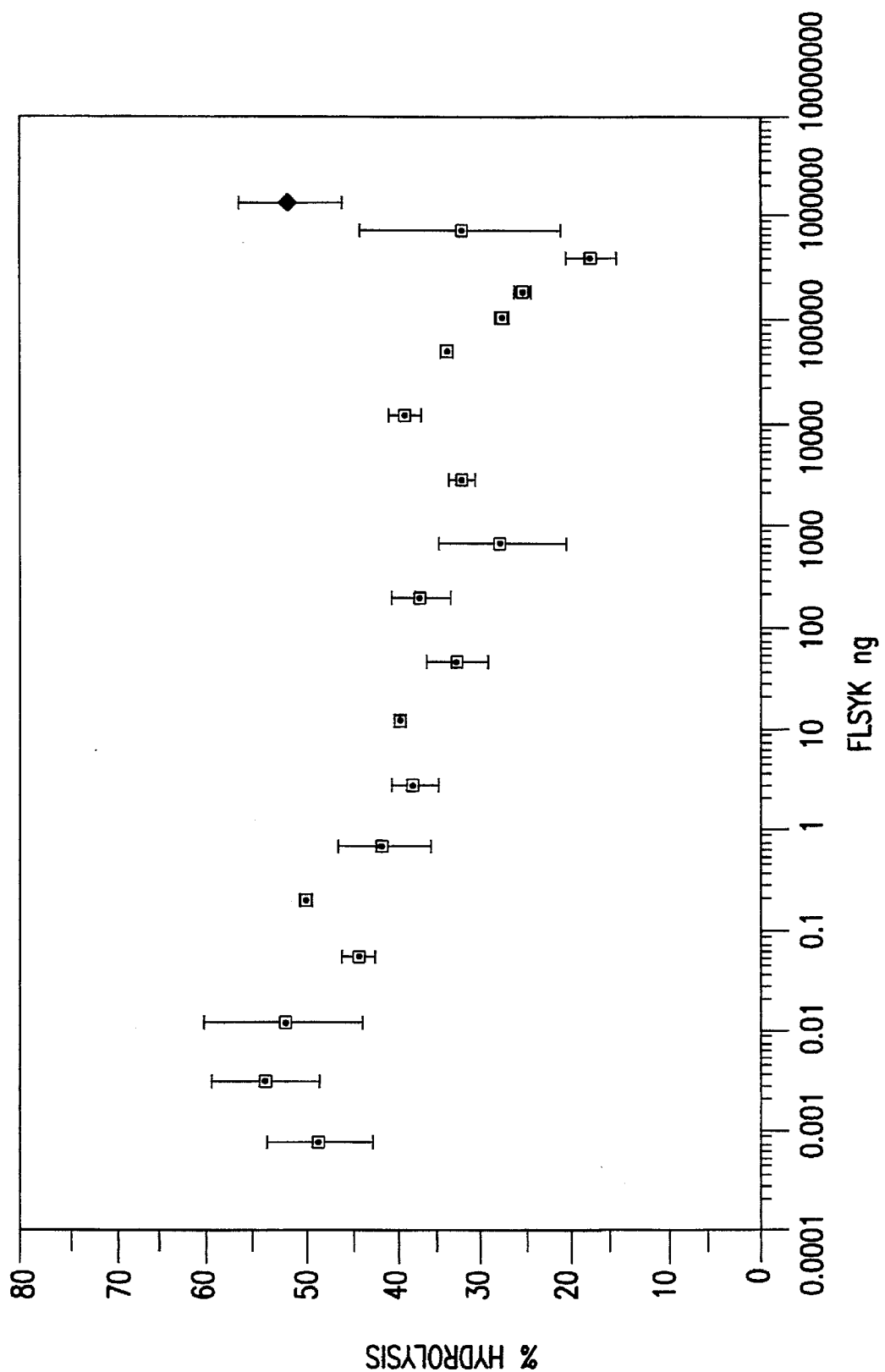

FIG. 4: Dose response curves for FLSYK (4a ▫ $PLA_2$ ♦ control) and WDIYR (4b ▫ snake (II) ♦ control) on human $PLA_2$ and snake (Crotalus Durissus) $PLA_2$ respectively. Both peptides occupy similar sites in their parent proteins and show inhibitory properties for the enzymatic activity.

Figure 5:
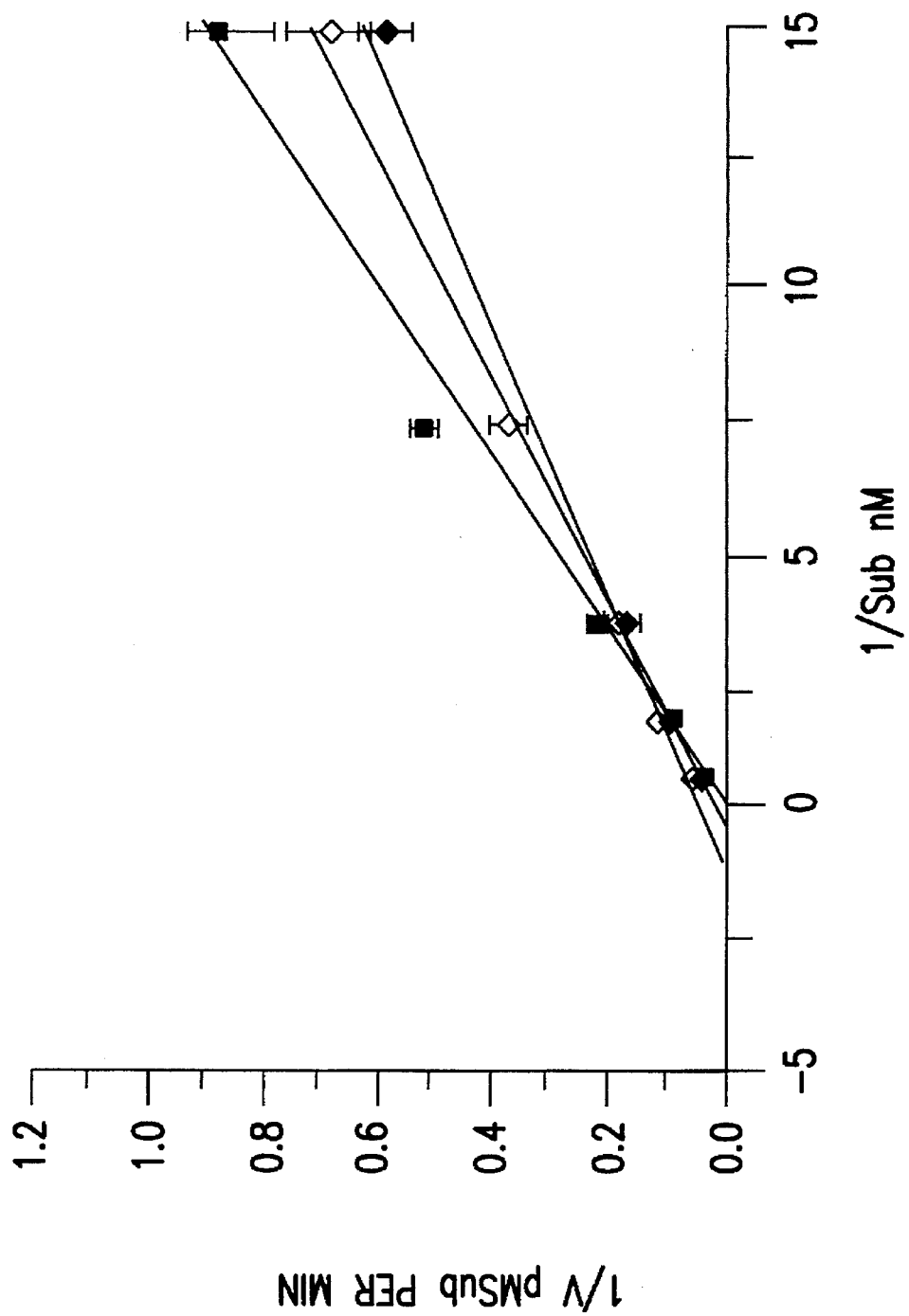

FIG. 5 shows a Lineweaver-Buspe plot showing inhibition of $PLA_2$ by FLSYK ($PLA_2$ ♦ 10 ug ■ FLSYK, ◊ 1 ug FLSYK).

Inhibition of PLA2 Activity

Proteins and Peptides

1. Synovial $PLA_2$, snake $PLA_2$ (Crotalus Durissus and Crotalus ATR?)
2. Phe-Leu-Ser-Tyr-Lys (FLSYK) (SEQ ID NO:8)
3. Acetyl-Phe-Leu-Ser-Tyr-Lys-Methyl ester (Ac-FLSYK-OMe)
4. Trp-Asp-Ile-Tyr-Arg (WDIYR) (SEQ ID NO:10)
5. Lys-Phe-Leu-Ser-Tyr (KFLSY) (SEQ ID NO:9)
6. Thr-Val-Ser-Tyr-Thr (TVSYT) (SEQ ID NO:12)
7. Phe-Lys-Thr-Tyr-Ser (FKTYS) (SEQ ID NO:13)
8. Thr-Glu-Ser-Tyr-Ser (TESYS) (SEQ ID NO:14)
9. Gly-Thr-Lys-Phe-Leu-Ser-Tyr-Lys-Phe-Ser-Asn (GTKFLSYKFSN) (SEQ ID NO:15)
10. Lys-Phe-Leu-Ser-Tyr-Tyr (KFLSYY) (SEQ ID NO:16)
11. Phe-Leu-Ser-Tyr (FLSY) (SEQ ID NO:17)
12. Phe-Leu-Ser-Tyr-Lys-$NH_2$ (FLSYK-$NH_2$)

Tryptic Digestion of PLA2:

Approximately 100 µg of PLA 2 was dissolved in 300 µl of 1 MTris pH 8.0 15 µl of Trypsin solution (10µ/1M Tris pH 8) was added and the peptide/trypsin solution was incubated for 2 hours at 37° C. 5 μl of neat TFA was used to lower the pH to terminate the digestion. The whole solution was subjected to microbore HPLC fractionation.

Microbore HPLC fractionation:

An ABI Microbore syringe pump system Model 140 was used. Detector wavelength was set at 220 nm at 0.5 aufs. A RP-300 1×100 mm was used. Fractionation was carried out by running a linear buffer gradient from 0.1% TFA in water to 0.1% TFA, 70% acetonitrile in water over sixty minutes. Amino acid sequences identified from fractions were:

Fraction #2 (K)YQYYSNK

Fraction #4 FLSYK

Fraction #5 FLSYK NLVNFHR

Fraction #7* EALLSYGFYG(C)H(C)GVGGR (C)(C) VTHD(C)(C)YK SQL(C)E(C)DK IT(C)AK AAAT(C) FAR

* peptides are held together by cystinyl bonds; ( ) denotes tentative assignment.

Fraction #9 EAALSYGFYG

Peptide Synthesis:

Peptide synthesis was carried out in an ABI Peptide Synthesiser Model 430A. T-Boc chemistry was used. HF cleavage was used to release peptide from the solid support.

PLA2 Serial Dilution:

Control: 10 μl of a standard $PLA_2$ solution was used at a concentration of 120 ng/10 μl in 20 mM Tris pH 8. Serial dilution was done by adding 20 mM Tris pH 8 buffer to the final volume of 20 μl.

Inhibitor solution: Pentapeptide was usually dissolved in 1 μl of 0.1% TFA solution and further 9 μl of 20 mM Tris pH8 was added. This solution was always maintained around pH7–8. 10 μl of this inhibitor solution was added into 10 μl of $PLA_2$ solution. Incubation: all samples were incubated at 37° C. for one hour.

$PLA_2$ solution: A standard PLA 2 solution was prepared in 20 mM Tris pH8.0 so that 10 μl will give 50% (approx) hydrolysis.

Pentapeptide solution: A standard pentapeptide solution was made to 10 mg/ml in 0.1% TFA. 100 μl was taken out and neutralised with 900 μl 20 mM Tris pH8. 10 μl (10 μg was taken out for dose response together with 10 μl of the $PLA_2$ solution). Serial dilution was carried out on 10 μl aliquots with 20 mM Tris pH 8.

Septic shock experiments:

Septic shock serum was diluted 1/100 for dose response experiments and used neat for serial dilution. Final reaction volume was always in the ratio of 10 μl serum/10 μl Tris or pentapeptide solution.

Activity assay:

$PLA_2$ activity was measured using a mixed micelle phosphatidylethanolamine (PE)/sodium deoxycholate assay, modified from a method described by Seilhamer et al (1). The PE substrate was prepared by dissolving freshly desiccated PE (Amersham, Bucks, England) in 2% DOC, then diluting this to 0.22 nmoles PE and 0.04% DOC per sample in assay buffer (50 mM Tris-HCl, pH 8.5, 2 mM calcium chloride, 150 mM sodium chloride, 0.04% DOC). The sample was prepared by mixing 10 μl of the test material with 10 μl mM Tris-HCl pH7.4 and leaving at 37° C. for 10 minutes. The reaction was started by the addition of 25 μl prewarmed substrate and terminated by addition of 10 μl 100 mM EDTA. The reaction mixture (30 μl was spotted and dried on silica TLC plates (Merck, Darmstadt, West Germany), and the plates were chromatographed using chloroform:methanol:acetic acid (90:10:1) as solvent. The dried plates were exposed overnight with Kodak X OMAT AR film. Radioactivity at the origin and of the liberated arachidonic acid was counted and the percent hydrolysis by PLA 2 determined.

A summary of the results obtained with peptides corresponding to residues 70–7u of several Type I and Type II enymes are set out in Table 1. These results show that there is considerable species specificity in that peptides active against one species of $PLA_2$ were not active against the other species tested. In addition none of the peptides tested were active against $PLA_2$ type 1. This result indicates that inhibition by peptides from this region of $PLA_2$ (70–74) appears to occur only on type II enymes.

Peptide 5 was shown to be an active inhibitor of human Type II $PLA_2$, however peptides 7, 8, 9, 10, 11 and 12 were all formed to be negative. This suggests that the peptide must be of a certain size to show inhibition and that inhibition will occur only with the specific sequence desired from the specific Type II enyme being tested.

TABLE 1

| Type Enzyme Inhibitor | II Syno $PLA_2$ | II Crot.Dur. $PLA_2$ | II Crot.Atr. $PLA_2$ | I N.N.Atra $PLA_2$ | I Por.Pan $PLA_2$ |
|---|---|---|---|---|---|
| sPLA₂ (FLSYK) | + | − | − | − | − |
| Crot.Dur (WDIYR) | − | + | − | − | − |
| Crot.Atr (TVSYT) | − | − | + | − | − |
| N.N.At (FKTYS) | − | − | − | − | − |
| Por.Pan (TESYS) | − | − | − | − | − | sPLA₂- Human Type II $PLA_2$
Crot.Dur- *Crotalus decrissurs* $PLA_2$
Crot.Atr- *Crotalus atrox* $PLA_2$
N.N.AT- *Naja naja atrox* $PLA_2$
Por.Pan.- Porcine pancreatic $PLA_2$ From the above results the present inventors believe that short peptides from the 70–74th region will most likely compete with the substrate for access to the active site and give inhibitory effects. It is believed that variation of the length of the peptides present in these regions may result in a optimisation of the inhibition.

The pentapeptide apparently possesses helical structure (approximately one and a half turns). Since the helical structures are stablised by hydrogen bonds between the C=O of one residue and NH of the fourth residue along the chain, the structure of the pentapeptide may be somewhat unstable and be more sensitive to the environment than a longer helical molecule. On the other hand, it would be expected that the range of sizes that is effective will be limited because of the limited access to the active site of $PLA_2$.

It is believed that the usual interchange of a hydrophobic residue e.g. Leu to Ile, Ser to Thr could also maintain the inhibitory effect. That is, amino acid residues alike in either charge or hydrophobicity could possibly be interchanged with those in the models without destroying the specific interaction of the two regions. Since helix-helix interactions are possibly the cause of the inhibitory action, small increases in the length of the peptides could stablise this structure.

The results obtained in these studies also suggest that monoclonal antibodies could be raised against epitopes containing one or both of the peptide regions to effect a similar result on the $PLA_2$ activity. Such monoclonal antibodies could be produced using standard techniques well known in the art.

As will be apparent to those skilled in the art the principle of the present invention will also have application for the inhibition of the activity of enzymes other than PLA$_2$ eg. the neuraminadase enzyme of the influenza virus or neuropeptide Y. It is envisaged that as biological active proteins in general, possess an active conformation which is stabilized by interaction with the surrounding chain of amino acids, that peptides adjacent to, and capable of interaction with the residues within the active site will inhibit the activity of the enzyme. It is intended that such other peptides are included within the scope of the present invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Johnson L. K. et al, Advance in Exp. Med & Biol; PLA 2 Role and Function in Inflammation, P. Y-K Wong ed, PLenum Press 17–34 (1991).
2. Scott D. L. et al, Science 250, 1563 (1990).
3. Seilhamer J. J. et al;, J. Biol Chem 264, 5335 (1989).
4. Renetseder R. et al, J. Biol Chem 260, 11627 (1985)
5. Scott D. L. et al, Science 250, 1541 (1990).
6. White S. P. et al, Science 250, 1560 (1990).
7. Prozanski W. et al, J. Rheumatol., 15:1351–1355 (1988)
8. Vadas P., J. Lab. Clin. Med., 104:873–881 (1984)

We claim:

1. A linear or cyclic peptide of at least 5 residues which inhibits the enzymatic activity of human synovial $PLA_2$, the peptide having the following formula:

$$A_1-A_2-A_3-A_4-A_5-A_6$$

in which $A_1$ is K or R or H or absent $A_2$ is F or Y or W $A_3$ is L or V or I or M $A_4$ is S or T $A_5$ is Y or F or W $A_6$ is K or R or H or absent.

2. A peptide as claimed in claim 1 in which the peptide is FLSYK or KFLSY.

3. A peptide as claimed in claim 1 in which the phospholipase $A_2$ is human phospholipase $A_2$.

4. A composition for use in treating the subject suffering from rheumatoid arthritis, septic shock and/or inflammatory disease, the composition comprising a therapeutically effective amount of the peptide as claimed in claim 1 and a pharmaceutically acceptable sterile carrier.

5. A peptide as claimed in claim 1, in which either $A_1$ or $A_6$ is absent.

6. A linear peptide which inhibits the enzymatic activity of *Crotalus durissus* $PLA_2$, the peptide having the following formula:

$$B_2-B_3-B_4-B_5-B_6$$

in which $B_2$ is W or F or Y $B_3$ is D or E $B_4$ is I or V or L or M $B_5$ is Y or F or W $B_6$ is R or K or H.

7. A peptide as claimed in claim 6 in which the peptide is WDIYR.

8. A linear peptide which inhibits the enzymatic activity of *Crotalus atrox* $PLA_2$, the peptide having the following formula:

$$C_2-C_3-C_4-C_5-C_6$$

in which $C_2$ is T or S $C_3$ is V or I or L or M $C_4$ is T or S $C_5$ is Y or F or W $C_6$ is T or S.

9. A peptide as claimed in claim 8 in which the peptide is TVSYT.

\* \* \* \* \*

UNITED STATES PATENT AND TRADEMARK OFFICE
CERTIFICATE OF CORRECTION

PATENT NO. : 5,656,602
DATED : August 12, 1997
INVENTOR(S) : Albert Peng Sheng Tseng et al.

It is certified that error appears in the above-identified patent and that said Letters Patent is hereby corrected as shown below:

On the title page, item [54] and column 1, line 1, the title should be
--PLA2 INHIBITORY COMPOUNDS--.

In the Claims:

Col. 19, line 41 (claim 1), "or cyclic" should be deleted.

Signed and Sealed this

Fourteenth Day of April, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 124 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ala Leu Trp Gln Phe Arg Ser Met Ile Lys Cys Ala Ile Pro Gly Ser
 1               5                  10                  15

His Pro Leu Met Asp Phe Asn Asn Tyr Gly Cys Tyr Cys Gly Leu Gly
                20                  25                  30

Gly Ser Gly Thr Pro Val Asp Glu Leu Asp Arg Cys Cys Glu Thr His
            35                  40                  45

Asp Asn Cys Tyr Arg Asp Ala Lys Asn Leu Asp Ser Cys Lys Phe Leu
    50                  55                  60

Val Asp Asn Pro Tyr Thr Glu Ser Tyr Ser Tyr Ser Cys Ser Asn Thr
65                  70                  75                  80

Glu Ile Thr Cys Asn Ser Lys Asn Asn Ala Cys Glu Ala Phe Ile Cys
                85                  90                  95

Asn Cys Asp Arg Asn Ala Ala Ile Cys Phe Ser Lys Ala Pro Tyr Asn
               100                 105                 110

Lys Glu His Lys Asn Leu Asp Thr Lys Lys Tyr Cys
           115                 120
```

( 2 ) INFORMATION FOR SEQ ID NO:2:

( i ) SEQUENCE CHARACTERISTICS:
    ( A ) LENGTH: 124 amino acids
    ( B ) TYPE: amino acid
    ( C ) STRANDEDNESS: single
    ( D ) TOPOLOGY: linear ( i i ) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

```
Ala Val Trp Gln Phe Arg Asn Met Ile Lys Cys Thr Ile Pro Gly Ser
 1               5                  10                  15

Asp Pro Phe Arg Glu Tyr Asn Asn Tyr Gly Cys Tyr Cys Gly Leu Gly
            20                  25                  30

Gly Ser Gly Thr Pro Val Asp Asp Leu Asp Arg Cys Cys Gln Thr His
        35                  40                  45

Asp His Cys Tyr Asn Gln Ala Lys Lys Leu Glu Ser Cys Lys Phe Leu
    50                  55                  60

Ile Asp Asn Pro Tyr Thr Asn Thr Tyr Ser Tyr Lys Cys Ser Gly Asn
65                  70                  75                  80

Val Ile Thr Cys Ser Asp Lys Asn Asn Asp Cys Glu Ser Phe Ile Cys
                85                  90                  95

Asn Cys Asp Arg Gln Ala Ala Ile Cys Phe Ser Lys Val Pro Tyr Asn
                100                 105                 110

Lys Glu Tyr Lys Asp Leu Asp Thr Lys Lys His Cys
            115                 120
```

(2) INFORMATION FOR SEQ ID NO:3:

(i) SEQUENCE CHARACTERISTICS:
      (A) LENGTH: 126 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

```
Ala Val Trp Gln Phe Arg Lys Met Ile Lys Cys Val Ile Pro Gly Ser
 1               5                  10                  15

Asp Pro Phe Leu Glu Tyr Asn Asn Tyr Gly Cys Tyr Cys Gly Leu Gly
            20                  25                  30

Gly Ser Gly Thr Pro Val Asp Glu Leu Asp Lys Cys Cys Gln Thr His
        35                  40                  45

Asp Asn Cys Tyr Asp Gln Ala Lys Lys Leu Asp Ser Cys Lys Phe Leu
    50                  55                  60

Leu Asp Asn Pro Tyr Thr His Thr Tyr Ser Tyr Ser Cys Ser Gly Ser
65                  70                  75                  80

Ala Ile Thr Cys Ser Ser Lys Asn Lys Glu Cys Glu Ala Phe Ile Cys
                85                  90                  95

Asn Cys Asp Arg Asn Ala Ala Ile Cys Phe Ser Lys Ala Pro Tyr Asn
                100                 105                 110

Lys Ala His Lys Asn Leu Asp Thr Lys Lys Tyr Cys Gln Ser
            115                 120                 125
```

(2) INFORMATION FOR SEQ ID NO:4:

(i) SEQUENCE CHARACTERISTICS:

(A) LENGTH: 124 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

| Asn | Leu | Val | Asn | Phe | His | Arg | Met | Ile | Lys | Leu | Thr | Thr | Gly | Lys | Glu |
|---|---|---|---|---|---|---|---|---|---|---|---|---|---|---|---|
| 1 | | | | 5 | | | | | 10 | | | | | 15 | |

| Ala | Ala | Leu | Ser | Tyr | Gly | Phe | Tyr | Gly | Cys | His | Cys | Gly | Val | Gly | Gly |
|---|---|---|---|---|---|---|---|---|---|---|---|---|---|---|---|
| | | | 20 | | | | | 25 | | | | | 30 | | |

| Arg | Gly | Ser | Pro | Lys | Asp | Ala | Thr | Asp | Arg | Cys | Cys | Val | Thr | His | Asp |
|---|---|---|---|---|---|---|---|---|---|---|---|---|---|---|---|
| | | 35 | | | | | 40 | | | | | 45 | | | |

| Cys | Cys | Tyr | Lys | Arg | Leu | Glu | Lys | Arg | Gly | Cys | Gly | Thr | Lys | Phe | Leu |
|---|---|---|---|---|---|---|---|---|---|---|---|---|---|---|---|
| | 50 | | | | | 55 | | | | | 60 | | | | |

| Ser | Tyr | Lys | Phe | Ser | Asn | Ser | Gly | Ser | Arg | Ile | Thr | Cys | Ala | Lys | Gln |
|---|---|---|---|---|---|---|---|---|---|---|---|---|---|---|---|
| 65 | | | | | 70 | | | | | 75 | | | | | 80 |

| Asp | Ser | Cys | Arg | Ser | Gln | Leu | Cys | Glu | Cys | Asp | Lys | Ala | Ala | Ala | Thr |
|---|---|---|---|---|---|---|---|---|---|---|---|---|---|---|---|
| | | | | 85 | | | | | 90 | | | | | 95 | |

| Cys | Phe | Ala | Arg | Asn | Lys | Thr | Thr | Tyr | Asn | Lys | Lys | Tyr | Gln | Tyr | Tyr |
|---|---|---|---|---|---|---|---|---|---|---|---|---|---|---|---|
| | | | 100 | | | | | 105 | | | | | 110 | | |

| Ser | Asn | Lys | His | Cys | Arg | Gly | Ser | Thr | Pro | Arg | Cys |
|---|---|---|---|---|---|---|---|---|---|---|---|
| | | 115 | | | | | 120 | | | | |

(2) INFORMATION FOR SEQ ID NO:5:

(i) SEQUENCE CHARACTERISTICS:
(A) LENGTH: 125 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:5:

| Ser | Leu | Leu | Glu | Phe | Gly | Gln | Met | Ile | Leu | Phe | Lys | Thr | Gly | Lys | Arg |
|---|---|---|---|---|---|---|---|---|---|---|---|---|---|---|---|
| 1 | | | | 5 | | | | | 10 | | | | | 15 | |

| Ala | Asp | Val | Ser | Tyr | Gly | Phe | Tyr | Gly | Cys | His | Cys | Gly | Val | Gly | Gly |
|---|---|---|---|---|---|---|---|---|---|---|---|---|---|---|---|
| | | | 20 | | | | | 25 | | | | | 30 | | |

| Arg | Gly | Ser | Pro | Lys | Asp | Ala | Thr | Asp | Glu | Cys | Cys | Val | Thr | His | Glu |
|---|---|---|---|---|---|---|---|---|---|---|---|---|---|---|---|
| | | 35 | | | | | 40 | | | | | 45 | | | |

| Cys | Cys | Tyr | Asn | Arg | Leu | Glu | Lys | Ser | Gly | Cys | Gly | Thr | Lys | Phe | Leu |
|---|---|---|---|---|---|---|---|---|---|---|---|---|---|---|---|
| | 50 | | | | | 55 | | | | | 60 | | | | |

| Thr | Tyr | Lys | Phe | Ser | Tyr | Arg | Gly | Gly | Gln | Ile | Ser | Cys | Ser | Thr | Asn |
|---|---|---|---|---|---|---|---|---|---|---|---|---|---|---|---|
| 65 | | | | | 70 | | | | | 75 | | | | | 80 |

| Gln | Asp | Ser | Cys | Arg | Lys | Gln | Leu | Cys | Gln | Cys | Asp | Lys | Ala | Ala | Ala |
|---|---|---|---|---|---|---|---|---|---|---|---|---|---|---|---|
| | | | | 85 | | | | | 90 | | | | | 95 | |

| Glu | Cys | Phe | Ser | Arg | Asn | Lys | Lys | Ser | Tyr | Ser | Leu | Lys | Tyr | Gln | Phe |
|---|---|---|---|---|---|---|---|---|---|---|---|---|---|---|---|
| | | | 100 | | | | | 105 | | | | | 110 | | |

| Tyr | Pro | Asn | Lys | Phe | Cys | Lys | Xaa | Xaa | Thr | Pro | Ser | Cys |
|---|---|---|---|---|---|---|---|---|---|---|---|---|

(2) INFORMATION FOR SEQ ID NO:6:

(i) SEQUENCE CHARACTERISTICS:
      (A) LENGTH: 47 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:6:

```
Asp Leu Leu Asn Phe Arg Lys Met Ile Lys Leu Lys Thr Gly Lys Ala
 1               5                  10                  15
Pro Val Pro Asn Tyr Ala Phe Tyr Gly Cys Tyr Cys Gly Leu Gly Gly
                20                  25                  30
Lys Gly Ser Pro Lys Asp Ala Thr Asp Xaa Cys Cys Ala Ala His
            35                  40                  45
```

(2) INFORMATION FOR SEQ ID NO:7:

(i) SEQUENCE CHARACTERISTICS:
      (A) LENGTH: 71 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:7:

```
His Leu Leu Asp Phe Arg Lys Met Ile Arg Tyr Thr Thr Gly Lys Glu
 1               5                  10                  15
Ala Thr Thr Ser Tyr Gly Ala Tyr Gly Cys His Cys Gly Val Gly Gly
                20                  25                  30
Arg Gly Ala Pro Lys Xaa Ala Lys Phe Leu Ser Tyr Lys Phe Ser Met
            35                  40                  45
Lys Lys Ala Ala Ala Ala Cys Phe Gln Phe Tyr Pro Ala Asn Arg Cys
    50                  55                  60
Ser Gly Arg Pro Pro Ser Cys
65                  70
```

(2) INFORMATION FOR SEQ ID NO:8:

(i) SEQUENCE CHARACTERISTICS:
      (A) LENGTH: 5 amino acids
      (B) TYPE: amino acid
      (C) STRANDEDNESS: single
      (D) TOPOLOGY: both (ii) MOLECULE TYPE: peptide (iii) HYPOTHETICAL: NO (iv) ANTI-SENSE: NO (v) FRAGMENT TYPE: N-terminal ( x i ) SEQUENCE DESCRIPTION: SEQ ID NO:8:

Phe Leu Ser Tyr Lys
1               5

( 2 ) INFORMATION FOR SEQ ID NO:9:

( i ) SEQUENCE CHARACTERISTICS:
( A ) LENGTH: 5 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

Lys Phe Leu Ser Tyr
1               5

( 2 ) INFORMATION FOR SEQ ID NO:10:

( i ) SEQUENCE CHARACTERISTICS:
( A ) LENGTH: 5 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:10:

Trp Asp Ile Tyr Arg
1               5

( 2 ) INFORMATION FOR SEQ ID NO:11:

( i ) SEQUENCE CHARACTERISTICS:
( A ) LENGTH: 5 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:11:

Thr Val Ser Tyr Thr
1               5

( 2 ) INFORMATION FOR SEQ ID NO:12:

( i ) SEQUENCE CHARACTERISTICS:
( A ) LENGTH: 5 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

Thr  Val  Ser  Thr  Thr
1                   5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:13:

Phe  Lys  Thr  Tyr  Ser
1                   5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:14:

Thr  Glu  Ser  Tyr  Ser
1                   5

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:15:

Gly  Thr  Lys  Phe  Leu  Ser  Tyr  Lys  Phe  Ser  Asn
1                   5                        10

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:16:

Lys Phe Leu Ser Tyr Tyr
    1                5

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:17:

Phe Leu Ser Tyr
    1